(12) United States Patent
Sobajima et al.

(10) Patent No.: US 9,993,289 B2
(45) Date of Patent: Jun. 12, 2018

(54) TREATMENT DEVICE

(71) Applicant: OLYMPUS CORPORATION, Tokyo (JP)

(72) Inventors: Hideo Sobajima, Sagamihara (JP); Tomoyuki Takashino, Fuchu (JP); Yusuke Takei, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 16 days.

(21) Appl. No.: 14/635,623

(22) PCT Filed: Mar. 7, 2014

(86) PCT No.: PCT/JP2014/056001
§ 371 (c)(1),
(2) Date: Mar. 2, 2015

(87) PCT Pub. No.: WO2014/148281
PCT Pub. Date: Sep. 25, 2014

(65) Prior Publication Data
US 2015/0374428 A1 Dec. 31, 2015

Related U.S. Application Data

(60) Provisional application No. 61/802,875, filed on Mar. 18, 2013.

(51) Int. Cl.
*A61B 18/14* (2006.01)
*A61B 17/32* (2006.01)
(Continued)

(52) U.S. Cl.
CPC .. *A61B 18/1445* (2013.01); *A61B 17/320092* (2013.01); *A61B 90/03* (2016.02);
(Continued)

(58) Field of Classification Search
None
See application file for complete search history.

(56) References Cited

U.S. PATENT DOCUMENTS

| | | | |
|---|---|---|---|
| 7,083,618 B2 * | 8/2006 | Couture | A61B 18/1445 606/49 |
| 7,329,257 B2 * | 2/2008 | Kanehira | A61B 17/3201 606/45 |

(Continued)

FOREIGN PATENT DOCUMENTS

| | | |
|---|---|---|
| EP | 1637086 A1 | 3/2006 |
| EP | 1 878 400 A1 | 1/2008 |

(Continued)

OTHER PUBLICATIONS

Oct. 27, 2016 Search Report issued in European Patent Application No. 14769158.8.

(Continued)

*Primary Examiner* — Ronald Hupczey, Jr.
(74) *Attorney, Agent, or Firm* — Oliff PLC

(57) ABSTRACT

A treatment device configured to hold a living tissue includes a swing member supported by a first grasping member and rotatable in a first direction and in an opposite direction opposite to the first direction. A support shaft of the swing member is supported on a side close to the distal end including a middle position between the distal end and the proximal end. A first holding surface is provided on the swing member close to a side of the second grasping member and grasps the living tissue. A second holding surface is provided on the second grasping member close to a side of the swing member and which faces the first holding surface and which is configured to hold the living tissue together with the first holding surface of the swing member.

6 Claims, 11 Drawing Sheets

(51) Int. Cl.
*A61B 90/00* (2016.01)
*A61B 17/29* (2006.01)

(52) U.S. Cl.
CPC ............... *A61B 2017/2936* (2013.01); *A61B 2017/2939* (2013.01); *A61B 2018/1455* (2013.01); *A61B 2090/035* (2016.02)

(56) References Cited

U.S. PATENT DOCUMENTS

| | | | |
|---|---|---|---|
| 7,566,334 B2* | 7/2009 | Christian | A61B 18/1442 606/205 |
| 8,444,642 B2* | 5/2013 | Contijoch | A61B 18/1442 606/51 |
| 8,754,229 B2* | 6/2014 | Epp | A01N 43/40 546/290 |
| 2006/0217697 A1 | 9/2006 | Lau et al. | |
| 2008/0015575 A1 | 1/2008 | Odom et al. | |
| 2009/0048595 A1 | 2/2009 | Mihori et al. | |
| 2010/0057082 A1 | 3/2010 | Hanna | |
| 2010/0057084 A1 | 3/2010 | Hanna | |
| 2010/0057117 A1 | 3/2010 | Yamada | |
| 2011/0184404 A1* | 7/2011 | Walberg | A61B 18/1445 606/33 |
| 2011/0278343 A1 | 11/2011 | Knodel et al. | |

FOREIGN PATENT DOCUMENTS

| | | |
|---|---|---|
| JP | 2009045456 A | 3/2009 |
| JP | 2010051779 A | 3/2010 |
| JP | 2010051802 A | 3/2010 |
| JP | 2012250079 A | 12/2012 |
| JP | 2012254324 A | 12/2012 |
| WO | 2010/088044 A2 | 8/2010 |

OTHER PUBLICATIONS

Oct. 1, 2015 International Preliminary Report on Patentability in PCT/JP2014/056001 (English translation only).

May 27, 2014 International Search Report issued in International Application No. PCT/JP2014/056001.

* cited by examiner

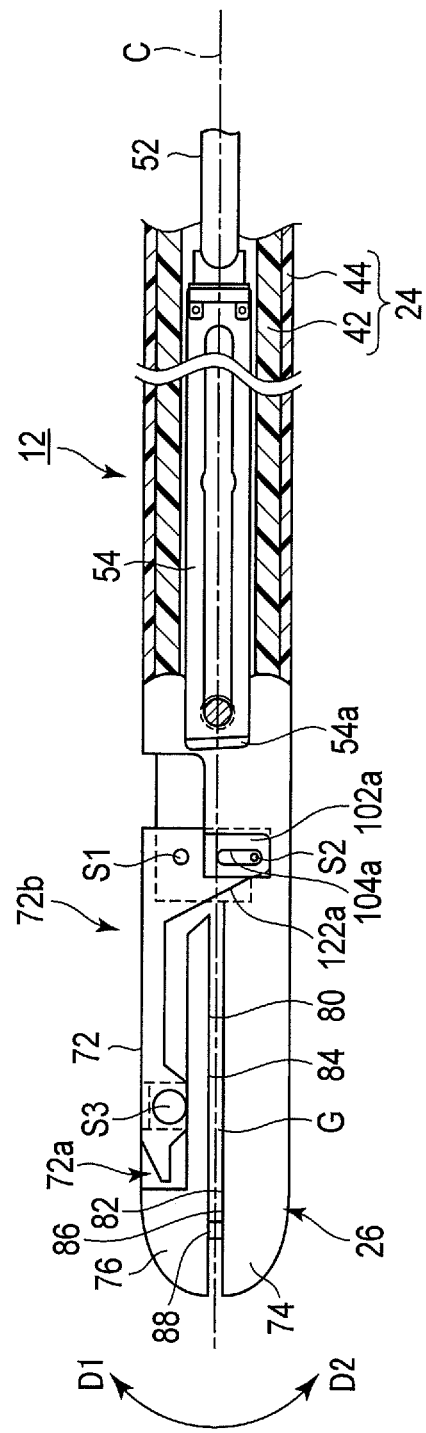
F I G. 2A

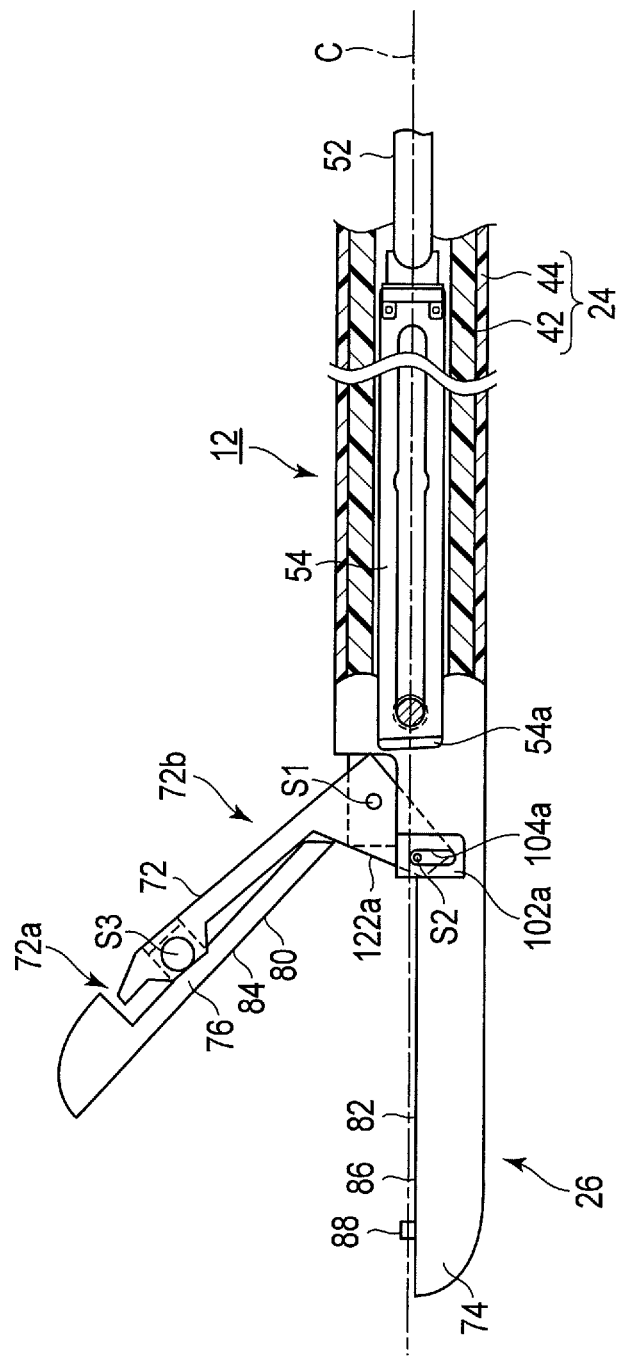
F I G. 2B

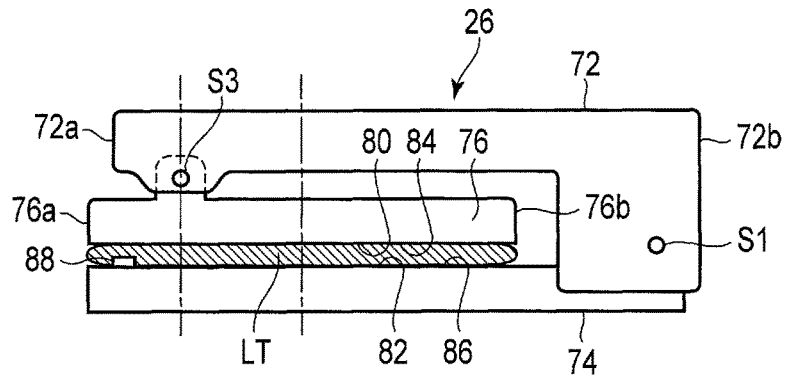
F I G. 7A
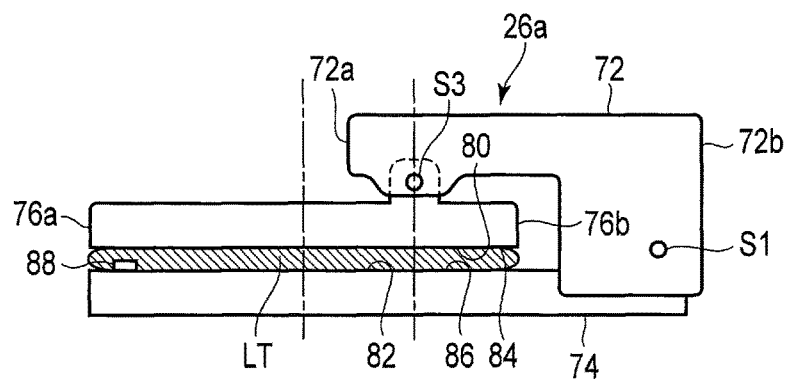
F I G. 7B
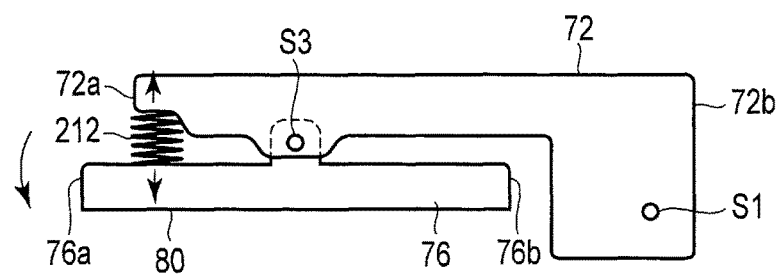
F I G. 8A

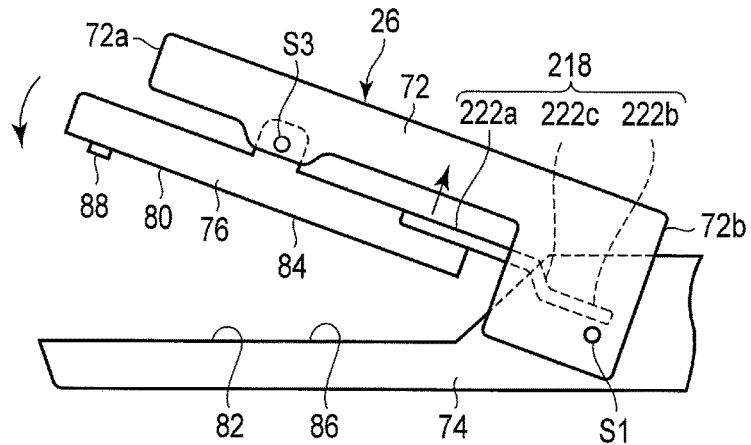
F I G. 9A
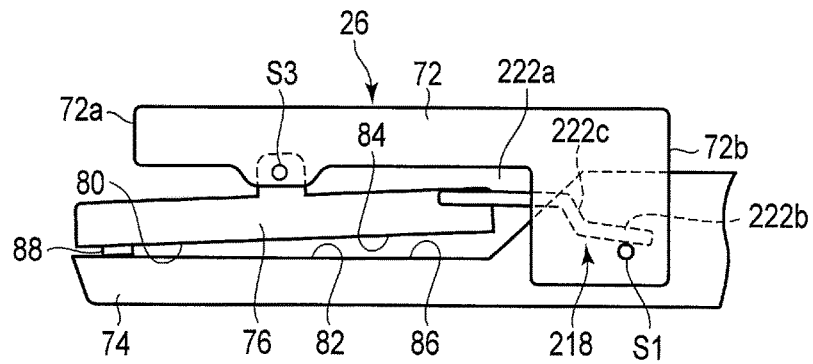
F I G. 9B
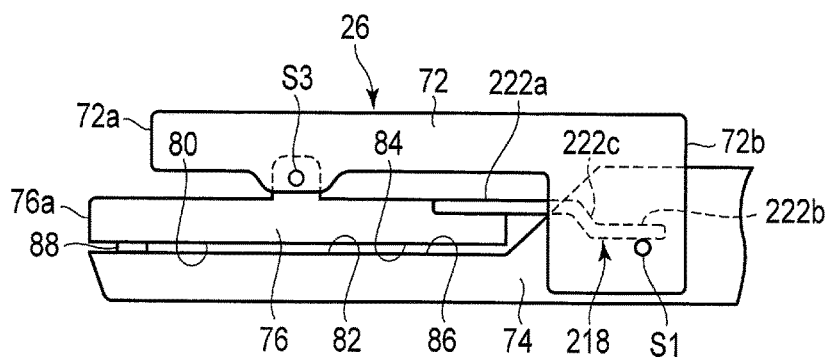
F I G. 9C

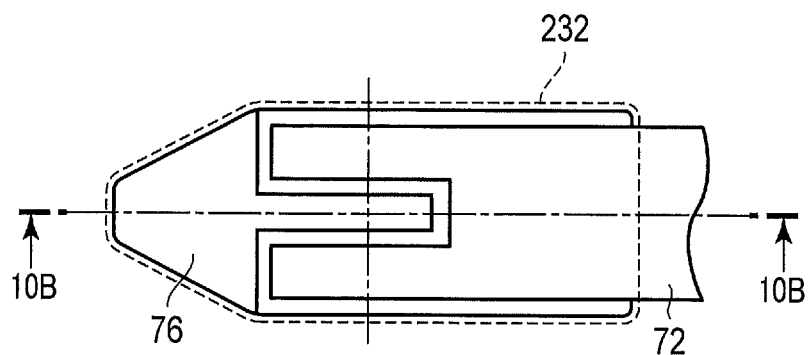
F I G. 10A
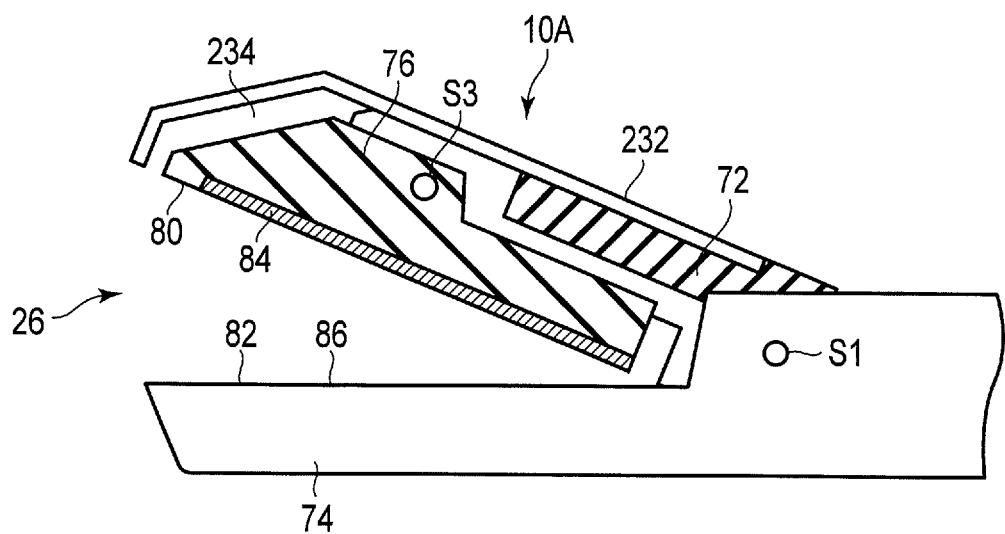
F I G. 10B

TREATMENT DEVICE

CROSS-REFERENCE TO RELATED APPLICATIONS

This application is a Continuation Application of PCT Application No. PCT/JP2014/056001, filed Mar. 7, 2014 and based upon and claiming the benefit of U.S. Provisional Application No. 61/802,875, filed Mar. 18, 2013, the entire contents of which are incorporated herein by reference.

BACKGROUND OF THE INVENTION

1. Field of the Invention

This invention relates to a treatment device including a holding surface to hold a living tissue.

2. Description of the Related Art

For example, US 2010/0057117 A1 has disclosed a first holding member which is openable and closable relative to a second holding member (probe). This first holding member is provided with a swing member having a living tissue holding surface to catch a living tissue between the first holding member and the second holding member. Thus, the living tissue can be grasped with more uniform force between the living tissue holding surface of the swing member and the living tissue holding surface of the second holding member.

BRIEF SUMMARY OF THE INVENTION

One aspect of treatment device according to the present invention, configured to hold a living tissue includes: first and second grasping members openable and closable relative to each other, each of first and second grasping members including a distal end portion, a proximal end portion, and a longitudinal axis defined by the distal end portion and the proximal end portion; a swing member supported between the distal end portion and the proximal end portion of the first grasping member, the swing member being rotatable in a first direction and in a second direction opposite to the first direction on a support shaft extending in a direction perpendicular to the longitudinal axis and in a direction that intersects at right angles with an open-close direction of the first and second grasping members, the swing member including a distal end close to the distal end portion of the first grasping member and a proximal end close to the proximal end portion of the first grasping member, the support shaft being supported on a side close to the distal end including a middle position between the distal end and the proximal end; a first holding surface which is provided on the swing member close to a side of the second grasping member and which is configured to hold the living tissue; and a second holding surface which is provided on the second grasping member close to a side of the swing member and which faces the first holding surface and which is configured to hold the living tissue in cooperation with the first holding surface of the swing member.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a schematic diagram showing structures of a shaft and a treatment portion of a treatment device according to the first embodiment, and showing how the treatment portion is closed;

FIG. 2B is a schematic diagram showing the structures of the shaft and the treatment portion of the treatment device according to the first embodiment, and showing how the treatment portion is opened;

FIG. 7A is a schematic diagram showing the relation between the first holding surface of the swing member and the second holding surface of the second grasping member in a condition in which the first grasping member of the treatment portion of the treatment device according to a modification of the first embodiment is closed relative to the second grasping member, and showing how the support shaft of the swing member is brought closer to the distal end side than the middle area between the distal end and the proximal end of the swing member;

FIG. 7B is an example of an undesirable treatment portion of the treatment device, and is a schematic diagram showing the relation between the first holding surface of the swing member and the second holding surface of the second grasping member in a condition in which the first grasping member is closed relative to the second grasping member, and showing how the support shaft of the swing member is brought closer to the proximal end side than the middle area between the distal end and the proximal end of the swing member;

FIG. 8A is a schematic diagram showing the relation between the first grasping member and the swing member of the treatment portion of the treatment device according to a second embodiment, and showing how the distal end portion of the first grasping member is coupled to the distal end of the swing member by a compression spring;

FIG. 9A is a schematic diagram showing how the first grasping member of the treatment portion of the treatment device according to the second embodiment is being closed relative to the second grasping member, and showing how an urging force is operated by the leaf spring to bring the proximal end of the swing member closer to the proximal end portion of the first grasping member;

FIG. 9B is a schematic diagram showing how the first grasping member of the treatment portion of the treatment device according to the second embodiment is being closed relative to the second grasping member, and showing how the urging force is operated by the leaf spring to bring the proximal end of the swing member closer to the proximal end portion of the first grasping member so that the distal end of the swing member rotates closer to the second grasping member and the proximal end of the swing member rotates away from the second grasping member;

FIG. 9C is a schematic diagram showing how the first grasping member of the treatment portion of the treatment device according to the second embodiment is closed relative to the second grasping member;

FIG. 10A is a schematic top view showing the location of a covering portion which covers the side of the first grasping member of the treatment portion of the treatment device according to a third embodiment opposite to the side where the first holding surface of the swing member is present; and FIG. 10B is a schematic longitudinal sectional view taken along the line 10B-10B in FIG. 10A, showing the location of the covering portion which covers the side of the first grasping member of the treatment portion of the treatment device according to the third embodiment opposite to the side where the first holding surface of the swing member is present.

DETAILED DESCRIPTION OF THE INVENTION

Hereinafter, embodiments of this invention will be described with reference to the drawings.

The first embodiment is described with reference to FIG. 1 to FIG. 7A.

Here, a linear type bipolar treatment device 12 to treat a living tissue, for example, through an abdominal wall is described by way of example as a treatment device (energy treatment instrument) which applies energy to the living tissue for a treatment of the living tissue.

Figure 1:
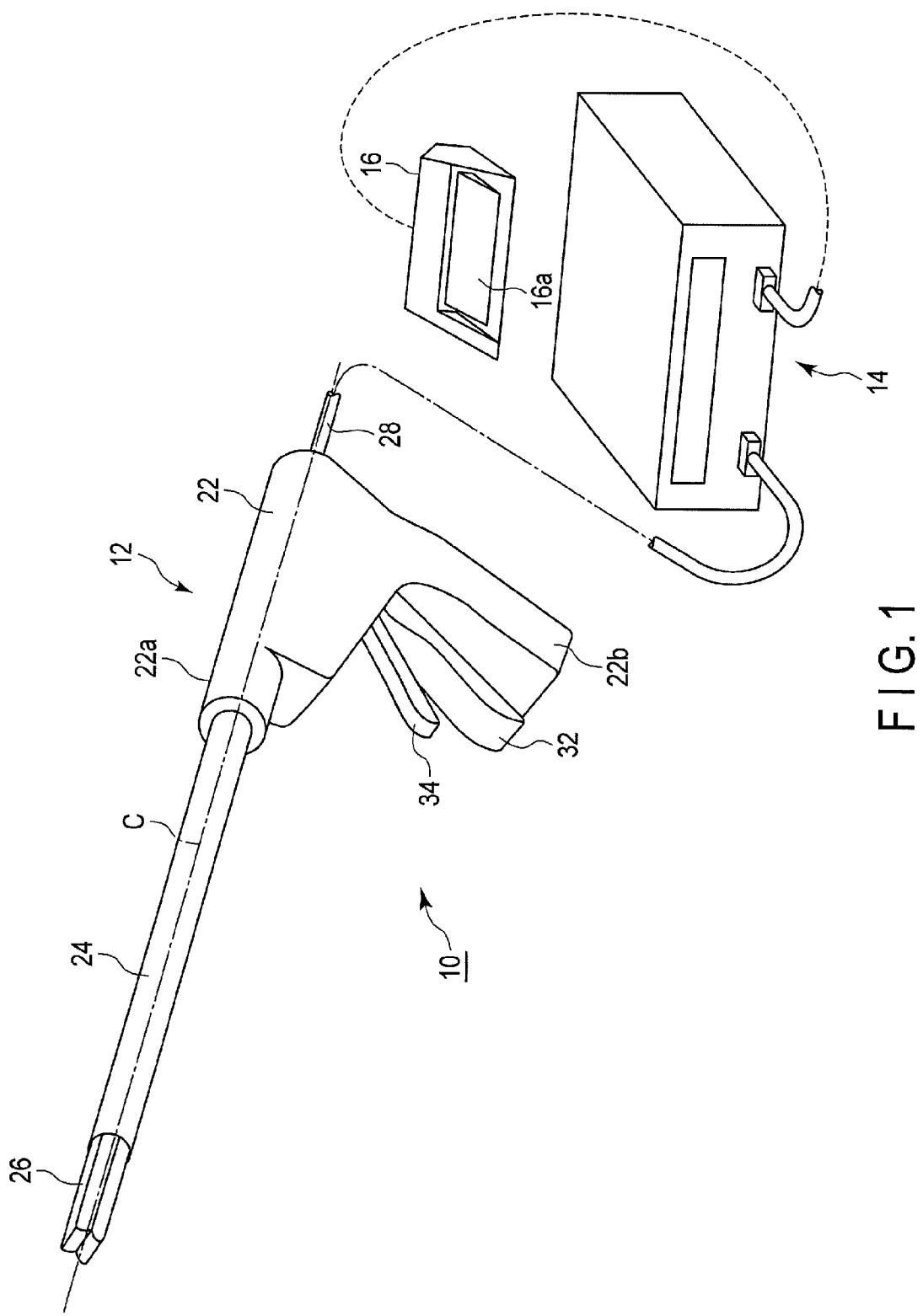
FIG. 1 is a schematic diagram showing a medical treatment system according to first to third embodiments.

As shown in FIG. 1, a medical treatment system 10 includes a treatment device (medical treatment instrument) 12, an energy source 14, and a foot switch 16 having a pedal 16a.

The treatment device 12 includes a handle 22, a shaft 24 having a central axis C, and a treatment portion 26. The energy source 14 is connected to the handle 22 via a cable 28. The foot switch 16 is connected to the energy source 14. A surgeon (user) operates the pedal 16a of the foot switch 16 by foot, and thereby switches on and off the supply of energy from the energy source 14 to the treatment portion 26 of the treatment instrument 12.

The handle 22 is substantially L-shaped. The shaft 24 is provided at one end (distal end) of the handle 22. For example, the above-mentioned cable 28 extends from the proximal end of the handle 22 which is substantially coaxial with the shaft 24.

The other end 22b of the handle 22 is a grasp portion to be grasped by the surgeon. The handle 22 includes a treatment portion open-close knob (first operation body) 32 provided in parallel with the other end 22b. According to this embodiment, the treatment portion open-close knob 32 is disposed in front of the other end 22b of the handle 22. The treatment portion open-close knob 32 is rotatable inside the handle 22 by an unshown pivot shaft, that is, can be brought closer to or away from the other end of the handle 22. The treatment portion open-close knob 32 is coupled to the proximal end of a later-described external cylinder 44 of the shaft 24 substantially in the central part of the handle 22. Therefore, if the treatment portion open-close knob 32 is brought closer to the other end 22b of the handle 22, the later-described external cylinder 44 of the shaft 24 is advanced relative to the handle 22 along its axial direction. On the other hand, if the treatment portion open-close knob 32 is brought away from the other end 22b of the handle 22, the later-described external cylinder 44 is retreated relative to the handle 22 along its axial direction.

The handle 22 further includes a cutter driving knob (second operation body) 34 provided in parallel with the treatment portion open-close knob 32 to move a later-described cutter 54. The cutter driving knob 34 is rotatable inside the handle 22 by an unshown pivot shaft, that is, can be brought closer to or away from the other end 22b of the handle 22. This cutter driving knob 34 is located in front of the treatment portion open-close knob 32, and coupled to the proximal end of a later-described drive rod 52. Thus, if the cutter driving knob 34 is brought closer to the other end of the handle 22, the drive rod 52 is advanced along its axial direction, and then the later-described cutter 54 is advanced. If the cutter driving knob 34 is brought away from the other end 22b of the handle 22, the drive rod 52 is retreated along its axial direction, and then the cutter 54 is retreated.

As shown in FIG. 2A and FIG. 2B, the shaft 24 includes an internal cylinder 42, and the external cylinder 44 slidably provided outside the internal cylinder 42. It is preferable that the central axes C of the internal cylinder 42 and the external cylinder 44 correspond to each other. It is preferable that the internal cylinder 42 and the external cylinder 44 have their inner circumferential surfaces and outer circumferential surfaces covered with a material having electrical insulating properties. The internal cylinder 42 is fixed in its proximal end portion to the handle 22. The external cylinder 44 is slidable along the axial direction of the internal cylinder 42.

Inside (cavity portion) the internal cylinder 42 of the shaft 24, the drive rod 52 is provided movably along its axial direction. It is preferable that the central axis C of the drive rod 52 corresponds to the central axis C of the shaft 24, that is, the internal cylinder 42 and the external cylinder 44. The thin plate-shaped cutter (treatment assistive device) 54 is provided at the distal end of the drive rod 52. The cutter 54 has an edge 54a formed at its distal end. Thus, the cutter driving knob 34 is operated so that the cutter 54 advances if the drive rod 52 is advanced or the cutter 54 retreats if the drive rod 52 is retreated. At the same time, the cutter 54 moves along later-described first and second cutter guide grooves (flow paths, fluid release grooves) 152 and 154 (see FIG. 4A to FIG. 5C). Particularly when the distal end of the cutter 54 has most advanced, the distal end of the cutter 54 is located slightly closer to the proximal end side than the distal ends of the cutter guide grooves 152 and 154. Depending on the degree at which a first grasping member 72 is opened relative to a later-described second grasping member 74 of the treatment portion 26, the distal end of the cutter 54 is set to be located inside the distal end of the internal cylinder 42 or located at the positions of the proximal ends of the cutter guide grooves 152 and 154 without contacting the living tissue when the distal end of the cutter 54 has most retreated.

As shown in FIG. 1 to FIG. 2B, the treatment portion 26 is provided at the distal end of the shaft 24. As shown in FIG. 2A and FIG. 2B, the treatment portion 26 includes the first and second grasping members 72 and 74, a swing member 76, first and second holding surfaces 80 and 82, first and second energy applying portions (high-frequency electrodes) 84 and 86, and a protrusion 88.

Each of the first and second grasping members 72 and 74 has electric insulating properties in at least its outer circumferential surface. Although the first grasping member 72 is openable and closable relative to the second grasping member 74 in the case described in this embodiment, a structure in which both the first and second grasping members 72 and 74 are openable and closable relative to each other may be used. Outer surfaces of the first and second grasping members 72 and 74 opposite to the first and second holding surfaces 80 and 82 are formed into smooth curved surfaces.

The distal end of the internal cylinder 42 has a swing supporting point S1 which rotatably supports the proximal end portion of the first grasping member 72. As shown in FIG. 2A, FIG. 2B, and FIG. 3B, the distal end of the external cylinder 44 located on the outer circumference of the external cylinder 44 has a pair of planes 102a and 102b (see FIG. 3B) which respectively have long holes 104a and 104b (see FIG. 2A and FIG. 2B) formed therein and which are parallel to each other. The long holes 104a and 104b are formed to be longer, for example, in a direction that deviates from the direction parallel to the central axis C. A later-described pair of arms 122a and 122b of the first grasping member 72 are movably supported by the long holes 104a and 104b between the pair of planes 102a and 102b. The second grasping member 74 is, for example, integrally provided at the distal end of the external cylinder 44.

The first grasping member 72 includes a distal end portion 72a, a proximal end portion 72b, and a longitudinal axis L1 defined by the distal end portion 72a and the proximal end portion 72b.

The proximal end portion 72b of the first grasping member 72 shown in FIG. 2A and FIG. 2B has a pair of arms 122a and 122b in a direction that deviates from the longitudinal axis L1. The pair of arms 122a and 122b of the first grasping member 72 are supported on the swing supporting point S1 rotatably relative to the distal end of the internal cylinder 42. The pair of arms 122a and 122b have action supporting points S2 movable in the long holes 104a and 104b at the distal end of the external cylinder 44. These action supporting points S2 respectively protrude outward from the pair of arms 122a and 122b. Thus, the action supporting points S2 of the pair of arms 122a and 122b are disposed between the planes 102a and 102b at the distal end of the external cylinder 44, and are movable in the long holes 104a and 104b of the planes 102a and 102b.

Therefore, when the external cylinder 44 is located at a position retreated relative to the internal cylinder 42, the first grasping member 72 is located at the closed position shown in FIG. 2A. When the external cylinder 44 is located at a position advanced relative to the internal cylinder 42, the first grasping member 72 is located at the opened position shown in FIG. 2B. Thus, the first grasping member 72 is openable and closable relative to the second grasping member 74.

Figure 3A:
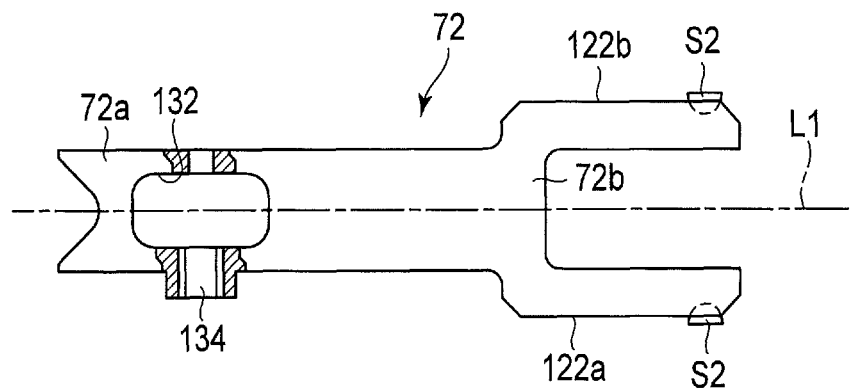
FIG. 3A is a schematic top view showing a first grasping member of the treatment portion of the treatment device according to the first embodiment.
Figure 3B:
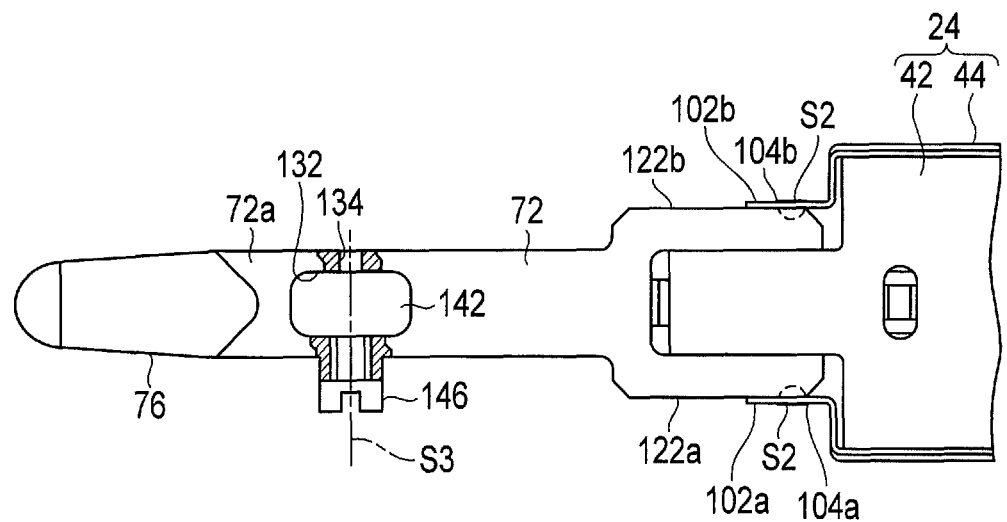
FIG. 3B is a schematic top view showing how a swing member is attached to the first grasping member of the treatment portion of the treatment device according to the first embodiment.

As shown in FIG. 3A, the distal end portion 72a of the first grasping member 72 has a support recess 132 which rotatably supports the swaying member 76, and a screw hole 134 which extends through the support recess 132. The screw hole 134 extends in a direction which intersects at right angles with the longitudinal axis L1 and which intersects at right angles with the open-close direction of the first and second grasping members 72 and 74.

Figure 4A:
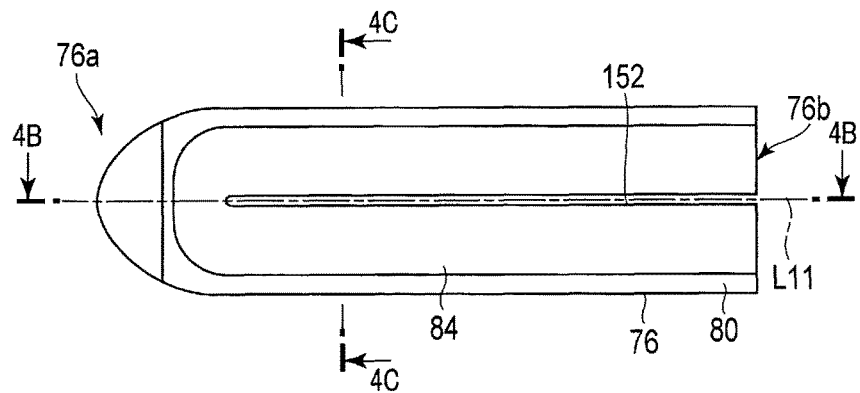
FIG. 4A is a schematic diagram showing the swing member of the treatment portion of the treatment device according to the first embodiment from a side of a first holding surface and a first high-frequency electrode.

As shown in FIG. 2A, FIG. 2B, and FIG. 3B, the swing member 76 made of a material having electric insulating properties and heat resisting properties is pivotally supported by the first grasping member 72 on a support shaft S3. As shown in FIG. 4A, the swing member 76 includes a distal end 76a, a proximal end 76b, and a longitudinal axis L11 defined by the distal end 76a and the proximal end 76b. The distal end 76a of the swing member 76 is located close to the distal end portion 72a of the first grasping member 72. The proximal end 76b of the swing member 76 is located close to the proximal end portion 72b of the first grasping member 72. The swing member 76 has a support projection 142 which rotates on the support shaft S3 extending in a direction perpendicular to the longitudinal axis L1 of the first grasping member 72 and the longitudinal axis L11 of the swing member 76 in a direction that intersects at right angles with the open-close direction of the first and second grasping members 72 and 74. The support projection 142 has a through-hole 144 around the support shaft S3. The support projection 142 of the swing member 76 is fitted to the support recess 132 of the first grasping member 72, and the screw hole 134 of the support recess 132 is aligned with the through-hole 144 of the support projection 142, and then a screw 146 is tightened. Thus, the swing member 76 is rotatable on the support shaft S3 in a first direction (clockwise direction) D1 and a second direction (counterclockwise direction) D2 in FIG. 4B. The case in which the swing member 76 rotates in the first direction (clockwise direction) D1 in FIG. 4B means, for example, a condition in which the distal end side of the swing member 76 has risen relative to the proximal end side while the first grasping member 72 is closed relative to the second grasping member 74. The case in which the swing member 76 rotates in the second direction (counterclockwise direction) D2 in FIG. 4B means, for example, a condition in which the distal end side of the swing member 76 has lowered relative to the proximal end side while the first grasping member 72 is closed relative to the second grasping member 74. It is preferable that the support shaft S3 of the swing member 76, the swing supporting point S1 at the distal end of the internal cylinder 42, and the action supporting point S2 at the distal end of the external cylinder 44 are parallel to one another.

Figure 6A:
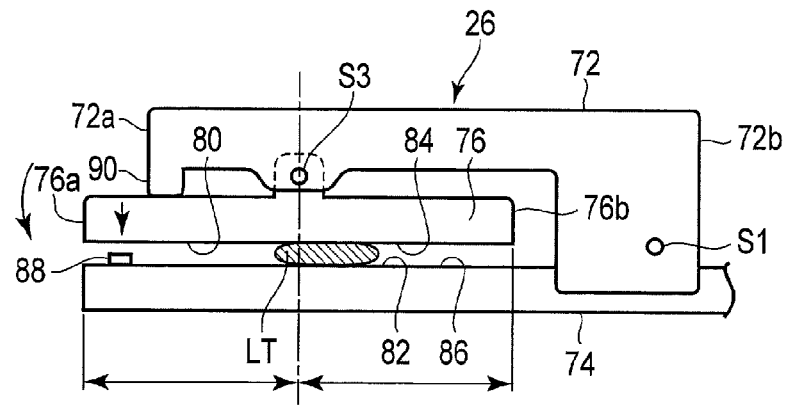
FIG. 6A is a schematic diagram showing how the first grasping member of the treatment portion of the treatment device according to the first embodiment is being closed relative to the second grasping member, and showing the moment when the first holding surface of the swing member has contacted a living tissue.

Here, the support shaft S3 is located at a middle position between the distal end 76a and the proximal end 76b of the swing member 76 along the longitudinal axis L11, or located on the side closer to the distal end 76a than the middle position. That is, the support shaft S3 is supported in an area close to the distal end 76a including the middle position between the distal end 76a and the proximal end 76b of the swing member 76. As schematically shown in FIG. 6A, it is described here that the support shaft S3 is located at the middle position between the distal end 76a and the proximal end 76b of the swing member 76 along the longitudinal axis L11.

Thus, when the first grasping member 72 is closed relative to the second grasping member 74 and the living tissue is grasped at a position closer to the proximal end 76b than the middle position of the longitudinal axis L11 between the distal end 76a and the proximal end 76b of the swing member 76, a moment is generated so that the distal end 76a of the swing member 76 can be closed after the proximal end 76b. That is, when the first grasping member 72 is closed relative to the second grasping member 74 so that the living tissue is grasped at a position closer to the proximal end side than the middle of the longitudinal direction of the first and second holding surfaces 80 and 82, the swing member 76 rotates in the second direction (counterclockwise direction) D2 in FIG. 4B.

Figure 4B:
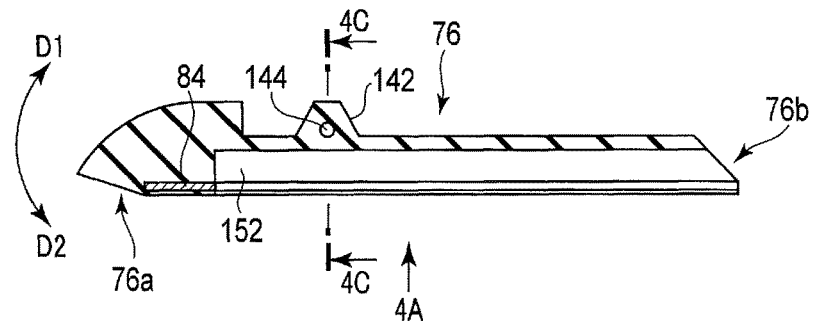
FIG. 4B is a schematic longitudinal sectional view of the swing member of the treatment portion of the treatment device according to the first embodiment taken along the line 4B-4B in FIG. 4A.
Figure 4C:
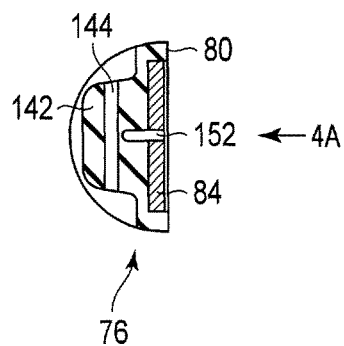
FIG. 4C is a schematic cross sectional view of the swing member of the treatment portion of the treatment device according to the first embodiment taken along the line 4C-4C in FIG. 4A and FIG. 4B.

As shown in FIG. 4B, the first holding surface 80 which cooperates with the later-described second holding surface 82 to grasp the living tissue is provided on the side of the swing member 76 closer to the second grasping member 74. Although the first holding surface 80 is formed as an outer edge of the swing member 76 in this embodiment, the first holding surface 80 is suitably changed depending on the shape and size of the first high-frequency electrode 84.

The thin plate-shaped first high-frequency electrode (first energy applying portion) 84 which applies high-frequency energy to the living tissue held between the first and second holding surfaces 80 and 82 to generate heat in the living tissue is fixed to the first holding surface 80. The surface of the first high-frequency electrode 84 is substantially U-shaped, and cooperates with the first holding surface 80 to form a first cutter guide groove (treatment assistive device guide groove) 152 to guide the cutter 54. That is, the first holding surface 80 and the first high-frequency electrode 84 have the linear first cutter guide groove (treatment assistive tool guide groove) 152 at a position along the central axis C. It is preferable that the width of the first cutter guide groove 152 is formed to be as small as possible.

Since the first high-frequency electrode 84 is substantially U-shaped, the distal end of the first high-frequency electrode 84 is closed in the vicinity of the distal end of the swing member 76, and the proximal end of the first high-frequency electrode 84 is divided into two parts in the vicinity of the proximal end of the swing member 76. Thus, the inside edge of the first high-frequency electrode 84 is formed as the cutter guide groove 152. It is preferable that the rear surface and outer edge of the first high-frequency electrode 84 are covered with the swing member 76.

Figure 5A:
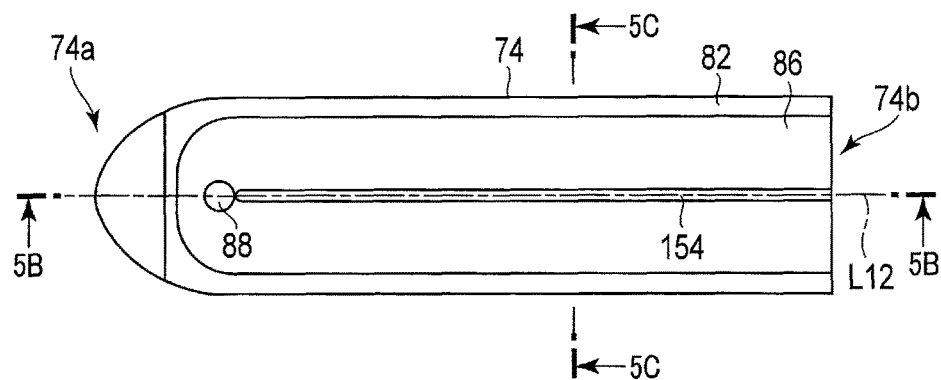
FIG. 5A is a schematic diagram showing a second grasping member of the treatment portion of the treatment device according to the first embodiment from the side of a second holding surface and a second high-frequency electrode.
Figure 5B:
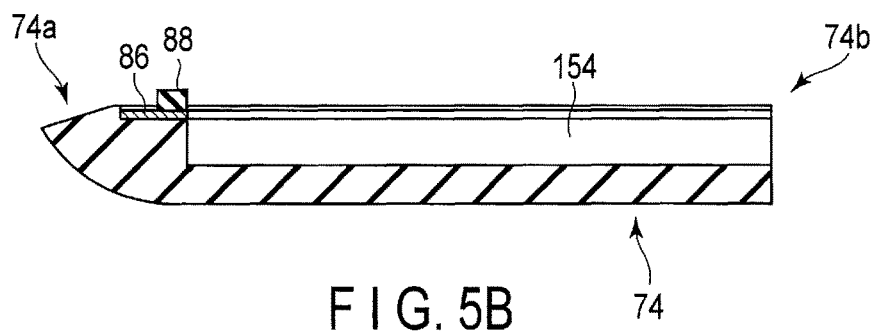
FIG. 5B is a schematic longitudinal sectional view of the second grasping member of the treatment portion of the treatment device according to the first embodiment taken along the line 5B-5B in FIG. 5A.
Figure 5C:
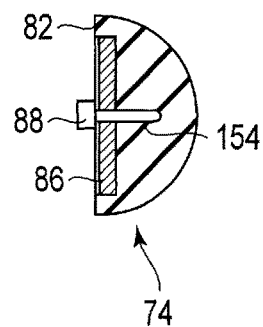
FIG. 5C is a schematic cross sectional view of the second grasping member of the treatment portion of the treatment device according to the first embodiment taken along the line 5C-5C in FIG. 5A.

As shown in FIG. 5A and FIG. 5B, the second grasping member 74 has a distal end portion 74a, a proximal end portion 74b, and a longitudinal axis L12 defined by the distal end portion 74a and the proximal end portion 74b. It is preferable that the second grasping member 74 is formed integrally with the distal end of the external cylinder 44.

On the side of the second grasping member 74 closer to the first grasping member 72 and the swing member 76, the second holding surface 82 which cooperates with the first holding surface 80 to grasp the living tissue is provided. Although the second holding surface 82 is formed as an outer edge of the second grasping member 74 in this embodiment, the second holding surface 82 is suitably changed depending on the shape and size of the second high-frequency electrode 86.

The thin plate-shaped second high-frequency electrode (second energy applying portion) 86 which applies high-frequency energy to the living tissue held between the first and second holding surfaces 80 and 82 to generate heat in the living tissue is fixed to the second holding surface 82. This second high-frequency electrode 86 is substantially U-shaped in the same manner as the first high-frequency electrode 84, and cooperates with the second holding surface 82 to form a second cutter guide groove (treatment assistive device guide groove) 154 to guide the cutter 54. That is, the second holding surface 82 and the second high-frequency electrode 86 have the linear second cutter guide groove (treatment assistive tool guide groove) 154 at a position along the central axis C. It is preferable that the width of the second cutter guide groove 154 is formed to be as small as possible.

Since the second high-frequency electrode 86 is substantially U-shaped, the distal end of the second high-frequency electrode 86 is closed in the vicinity of the distal end of the second grasping member 74, and the proximal end of the second high-frequency electrode 86 is divided into two parts in the vicinity of the proximal end of the second grasping member 74. Thus, the inside edge of the second high-frequency electrode 86 is formed as the cutter guide groove 154. It is preferable that the rear surface and outer edge of the second high-frequency electrode 86 are covered with the second grasping member 74.

The first high-frequency electrode 84 is electrically connected to the energy source 14 by an unshown conducting wire through the internal cylinder 42 or between the internal cylinder 42 and the external cylinder 44 and through the cable 28. The second high-frequency electrode 86 is electrically connected to the energy source 14 by an unshown conducting wire through the internal cylinder 42 or between the internal cylinder 42 and the external cylinder 44 and through the cable 28. Thus, if energy is supplied from the energy source 14 while the living tissue is being held between the first and second holding surfaces 80 and 82, that is, held between the first and second high-frequency electrodes 84 and 86, the living tissue held between the first and second high-frequency electrodes 84 and 86 can be, for example, coagulated or sealed and then treated.

It is preferable that the first and second high-frequency electrodes 84 and 86 are formed to be longer in a direction parallel to the longitudinal axis L than in a direction perpendicular to the longitudinal axis L. In this case, the living tissue disposed between the first and second high-frequency electrodes 84 and 86 can be continuously and seamlessly sealed. The sealed living tissue can be separated into two parts by guiding the cutter 54 through the first and second cutter guide grooves 152 and 154.

Here, according to this embodiment, the protrusion (spacer) 88 is provided on the surface of the second high-frequency electrode 86 to maintain a distance between the first high-frequency electrode 84 and the second high-frequency electrode 86 and prevent contact while the first and second grasping members 72 and 74 are closed. The protrusion 88 is made of a material having heat resisting properties and electric insulating properties. For example, a resin material such as PTFE and PEEK, ceramics, or a material such as PTFE having heat resisting properties and electric insulating properties which covers the periphery of a metallic material is used for the protrusion 88. When the resin material is used, the height and hardness are adjusted in consideration of the deformation of the resin material pressed by the first high-frequency electrode 84 and the living tissue.

As shown in FIG. 5A and FIG. 5B, it is preferable that the protrusion 88 is located close to the distal end of the second cutter guide groove 154. It is also preferable that the protrusion 88 is located at a position that does not prevent the second high-frequency electrode 86 from seamlessly and continuously sealing the living tissue. According to this embodiment, the protrusion 88 is located in the vicinity of the distal end portion of the surface of each of the first and second high-frequency electrodes 84 and 86 and located closer to its inner edge (second cutter guide groove 154) than its outer edge.

One protrusion 88 is not exclusively provided. More than one protrusion 88, for example, two protrusions 88 may be provided as long as the protrusions do not prevent the second high-frequency electrode 86 from seamlessly and continuously sealing the living tissue. In FIG. 5B, the protrusion 88 is mounted on the second high-frequency electrode 86 in a fixed state. However, it is also preferable that the protrusion 88 is fixed to the second grasping member 74 through the second high-frequency electrode 86 because the protrusion 88 has heat resisting properties and electric insulating properties.

The first and second cutter guide grooves 152 and 154 are also used as fluid release grooves which are in communication with the inside of the internal cylinder 42 where the drive rod 52 of the cutter 54 is provided and which receive a fluid generated from the living tissue.

In this embodiment, it is preferable that a restriction portion 90 is formed in the distal end portion 72a of the first grasping member 72. The restriction portion 90 can inhibit, that is, limit the clockwise rotation of the swing member 76 in FIG. 6A. The restriction portion 90 is not exclusively formed in the distal end portion 72a of the first grasping member 72, and it is also preferable that the restriction portion 90 is formed in the swing member 76.

Therefore, the treatment portion 26 according to this embodiment has the structure described below.

The first grasping member 72 includes the distal end portion 72a, the proximal end portion 72b, and the longitudinal axis L1 defined by the distal end portion 72a and the proximal end portion 72b. The swing member 76 is supported between the distal end portion 72a and the proximal end portion 72b of the first grasping member 72. The swing member 76 is rotatable in the first direction D1 and in the second direction D2 opposite to the first direction D1 on the support shaft S3 extending in a direction perpendicular to the longitudinal axis L11 and in a direction that intersects at right angles with the open-close direction of the first and second grasping members 72 and 74. That is, the first grasping member 72 and the swing member 76 form what is known as a seesaw jaw. The support shaft S3 of the swing member 76 is supported at the middle position between the distal end 76a and the proximal end 76b of the swing member 76. The first holding surface 80 is provided on the side of the swing member 76 closer to the second grasping member 74, and can grasp the living tissue. The second holding surface 82 is provided on the side of the second grasping member 74 closer to the swing member 76, faces the first holding surface 80, and can cooperate with the first holding surface 80 of the swing member 76 to grasp the living tissue.

The treatment portion 26 of the treatment device 12 according to this embodiment has the first and second high-frequency electrodes 84 and 86 which are provided in the first and second holding surfaces 80 and 82 and which apply energy to the living tissue held between the first and second holding surfaces 80 and 82, and also has the protrusion 88 which is provided in the second holding surface 82 and which forms a clearance between the first and second holding surfaces 80 and 82 when the first and second holding surfaces 80 and 82 are closed relative to each other.

The treatment portion 26 of the treatment device 12 according to this embodiment also includes the cutter (treatment assistive tool) 54 which is movable between the position located between the swing member 76 and the second grasping member 74 and the position to escape from the position located between the swing member 76 and the second grasping member 74, the first cutter guide groove 152 which is provided in the first holding surface 80 and which guides the cutter 54 between the first and second holding surfaces 80 and 82, and the second cutter guide groove 154 which is provided in the second holding surface 82 and which cooperates with the first cutter guide groove 152 to guide the cutter 54.

Next, the function of the medical treatment system 10 according to this embodiment is described.

As shown in FIG. 2A, the treatment portion 26 is inserted into a lumen such as a body cavity while the first grasping member 72 is closed relative to the second grasping member 74. The treatment portion 26 is then placed to face a living tissue to be treated. The treatment portion open-close knob 32 of the handle 22 is pulled to advance the external cylinder 44 relative to the internal cylinder 42. Thus, as shown in FIG. 2B, the first grasping member 72 is opened relative to the second grasping member 74. In this state, the living tissue to be treated is disposed between the first and second holding surfaces 80 and 82. That is, the living tissue to be treated is disposed between the first and second high-frequency electrodes 84 and 86. In this state, the treatment portion open-close knob 32 located before the handle 22 is moved forward, and the external cylinder 44 is retreated relative to the internal cylinder 42. Thus, as shown in FIG. 2A, the first grasping member 72 is closed relative to the second grasping member 74. That is, the living tissue to be treated is held between the first and second high-frequency electrodes 84 and 86.

The treatment portion 26 of the treatment device 12 according to this embodiment grasps the living tissue to be treated, for example, at the position closer to the proximal end 76b than the middle part between the distal end 76a and the proximal end 76b of the first holding surface 80 of the swing member 76 and in the second holding surface 82 facing the first holding surface 80. When a grasp force is applied to the living tissue from the condition in which the protrusion 88 provided in the surface of the second holding surface 82 or the second high-frequency electrode 86 has separated from the first holding surface 80 or the first high-frequency electrode 84 and the condition in which the first and second holding surfaces 80 and 82 are parallel to each other, the first holding surface 80 moves in a manner shown from FIG. 6A to FIG. 6C.

FIG. 6A shows the moment when a living tissue $L_T$ is brought into contact with both the first and second holding surfaces 80 and 82. In the state shown in FIG. 6A, the first grasping member 72 is urged to be closed relative to the second grasping member 74.

Figure 6B:
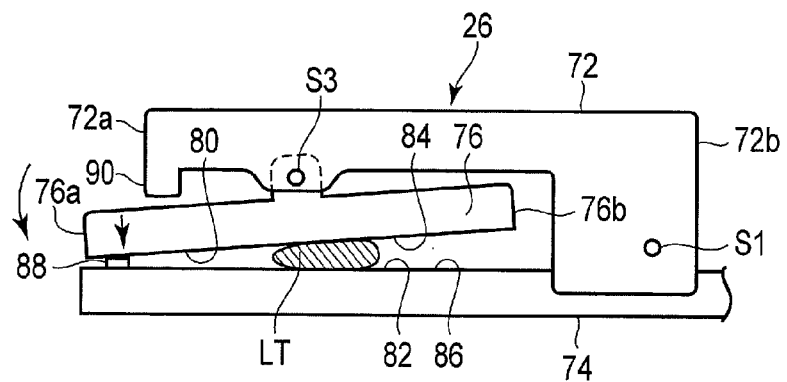
FIG. 6B is a schematic diagram showing how the first grasping member of the treatment portion of the treatment device according to the first embodiment is being closed relative to the second grasping member, and showing how the first holding surface of the swing member has contacted the living tissue and then the distal end of the swing member has rotated closer to the second grasping member, and the proximal end of the swing member has rotated away from the second grasping member.

As shown in FIG. 6B, when the swing member 76, that is, the first holding surface 80 is moved to press the living tissue $L_T$ between the first holding surface 80 and the second holding surface 82, a turning moment on the swing supporting point S1 at the distal end of the internal cylinder 42 is greater on the distal end side of the support shaft S3 than on the proximal end side. Thus, the living tissue $L_T$ is pressed while the distal end side of the support shaft S3 of the distal end side of the swing member 76 falls and the proximal end side rises. That is, the distal end 76a of the swing member 76 comes closer to the second holding surface 82 before the proximal end 76b. In this way, the living tissue $L_T$ is pressed while the distal end side of the support shaft S3 of the swing member 76 falls and the proximal end side rises, so that the escape of the living tissue $L_T$ to the distal end side is prevented, and force is applied to the living tissue $L_T$ toward the lower side of the second holding surface 82 (closing direction of the first grasping member 72) or toward the proximal end side of the second grasping member 74. Therefore, force is applied to move the living tissue $L_T$ toward the proximal end sides of the swing member 76 and the second grasping member 74 at the moment when the living tissue $L_T$ is held between the first and second holding surfaces 80 and 82.

Figure 6C:
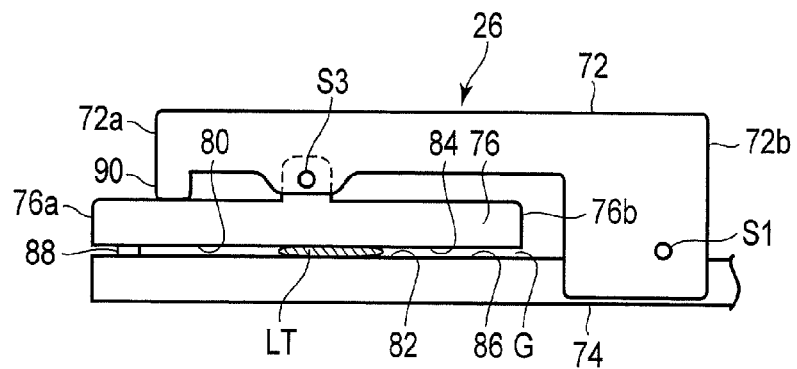
FIG. 6C is a schematic diagram showing how the first grasping member of the treatment portion of the treatment device according to the first embodiment is closed relative to the second grasping member, and the living tissue is then held between the first holding surface of the swing member and the second holding surface of the second grasping member.

As shown in FIG. 6C, the swing member 76 rotates around the support shaft S3 due to a reaction force from the living tissue $L_T$ as a press force (holding force) applied to the living tissue $L_T$ between the first and second holding surfaces 80 and 82 increases. At this point, the swing member 76 rotates in a clockwise direction D1. Thus, when the first and second holding surfaces 80 and 82 are completely closed, the living tissue $L_T$ is grasped with a uniform holding force.

In this way, when the first grasping member 72 is closed relative to the second grasping member 74, the distal end 76a of the swing member 76 closes relative to the second holding surface 82 earlier than the proximal end 76b. Thus, while the swing member 76 is rotating so that the first holding surface 80 or the first high-frequency electrode 84 is closed relative to the second holding surface 82 or the second high-frequency electrode 86, the first holding surface 80 or the first high-frequency electrode 84 grasps the living tissue with a uniform grasp force immediately after applying a force to the living tissue in a direction perpendicular to the surface of the second holding surface 82 or the second high-frequency electrode 86 (particularly in the closing direction of the first grasping member 72) or toward the proximal end side of the second grasping member 74.

While the living tissue is held between the first and second holding surfaces 80 and 82, a space G is maintained between the first and second high-frequency electrodes 84 and 86 by the protrusion 88 and the restriction portion 90 to prevent the first and second high-frequency electrodes 84 and 86 from contacting each other and causing a short circuit.

While the living tissue to be treated is caught to maintain the space G between the first and second high-frequency electrodes 84 and 86, the pedal 16a of the foot switch 16 is depressed by the foot. Accordingly, high-frequency energy is applied to the living tissue between the first and second high-frequency electrodes 84 and 86 from the energy source 14 to heat the living tissue and then coagulate the living tissue. At this point, the living tissue is coagulated regardless of the widths of the first and second cutter guide grooves 152 and 154 because the widths of the cutter guide grooves 152 and 154 are formed to be narrow. The cutter 54 is then moved along the cutter guide grooves 152 and 154 as needed to cut the treated living tissue.

As described above, the following can be said according to this embodiment.

In the treatment portion 26 of the treatment device 12 according to this embodiment, the rotary member 76 is pivotally supported by the first grasping member 72 on the support shaft S3, and the first grasping member 72 and the rotary member 76 form what is known as a seesaw jaw. Thus, the amount of holding force to hold the living tissue between the first holding surface 80 and the first high-frequency electrode 84 of the swing member 76 and the second holding surface 82 and the second high-frequency electrode 86 of the second grasping member 74 can be uniform.

When the swing member 76 is rotated to close the first holding surface 80 relative to the second holding surface 82, the distal end 76a of the swing member 76 can be brought closer to the second holding surface 82 earlier than the proximal end 76b. Thus, it is possible to inhibit the living tissue from escaping to the distal end side of the swing member 76 when the living tissue is grasped. That is, when performing the operation of grasping the living tissue, the treatment device 12 according to this embodiment can maximally prevent the living tissue from escaping to the side of the distal end 76a of the swing member 76 and the distal end side of the second grasping member 74, that is, the distal end side of the first and second holding surfaces 80 and 82.

When the first holding surface 80 is closed relative to the second holding surface 82, the protrusion 88 and the limiting portion 90 can prevent the first and second high-frequency electrodes 84 and 86 from contacting each other. In addition, the protrusion 88 also has an anti-slip function, so that it is possible to inhibit the living tissue from slipping toward the distal end side and proximal end side of the first and second holding surfaces 80 and 82.

In the example described according to this embodiment, the support shaft S3 is disposed substantially in the middle part between the distal end 76a and the proximal end 76b of the swing member 76, that is, substantially in the middle part between the distal end 76a and the proximal end 76b of the first holding surface 80. Alternatively, it is also preferable that the support shaft S3 is disposed between the middle part between the distal end 76a and the proximal end 76b of the swing member 76, and the distal end 76a of the swing member 76. In the case of the structure of the treatment portion 26 shown in FIG. 7A, the living tissue is grasped from the position closer to the distal end 76a including the middle part between the distal end 76a and the proximal end 76b of the first holding surface 80 to the position close to the proximal end 76b. Since the support shaft S3 is located closer to the distal end side than the middle part between the distal end 76a and the proximal end 76b of the first holding surface 80, the first holding surface 80 contacts the living tissue, and the swing member 76 rotates around the support shaft S3 (counterclockwise around the support shaft S3 in FIG. 7A), so that the distal end 76a of the first holding surface 80 comes closer to the second holding surface 82 than the proximal end 76b. Thus, the escape of the living tissue to the distal end side relative to the first holding surface 80 is prevented. When the first holding surface 80 is brought close to the second holding surface 82, the living tissue can be grasped with a uniform grasp force.

An example of an undesirable treatment portion 26a is shown in FIG. 7B. The support shaft S3 is disposed between the middle part between the distal end 76a and the proximal end 76b of the swing member 76, and the proximal end 76b of the swing member 76. When the living tissue is grasped from the position close to the distal end 76a including the middle part between the distal end 76a and the proximal end 76b of the first holding surface 80 to the position close to the proximal end 76b, the swing member 76 rotates around the support shaft S3 (clockwise around the support shaft S3 in FIG. 7B), so that the distal end 76a of the first holding surface 80 comes farther away from the second holding surface 82 than the proximal end 76b. Thus, if the treatment portion 26a shown in FIG. 7B is used, the distal end 76a of the first holding surface 80 easily rises relative to the proximal end 76b, and the living tissue is more easily pushed out to the distal end side of the first holding surface 80.

Next, the second embodiment is described with reference to FIG. 8A to FIG. 9C. This embodiment is a modification of the first embodiment. The same components as the components described in the first embodiment or the components having the same functions are provided with the same signs wherever possible, and detailed explanations thereof are omitted.

Although the support shaft S3 is located in between the distal end 76a and the proximal end 76b of the swing member 76 in the example illustrated in FIG. 8A to FIG. 8D, the support shaft S3 may be located at a position closer to the distal end 76a than midway between the distal end 76a and the proximal end 76b of the swing member 76 as shown in FIG. 7A. That is, the support shaft S3 is located on the distal end side including the middle of the swing member 76.

The treatment portion 26 shown in FIG. 8A has a compression spring (elastic member) 212 disposed between the distal end portion 72a of the first grasping member 72 and the distal end 76a of the swing member 76. The compression spring 212 urges the distal end 76a of the swing member 76 to come closer to the second grasping member 74 than the proximal end 76b of the swing member 76 by the distal end portion 72a of the first grasping member 72. That is, the compression spring 212 is disposed between the side closer to the distal end portion 72a of the first grasping member 72 than the support shaft S3 and the side close to the distal end 76a of the swing member 76, and brings the side close to the distal end portion 72a of the first grasping member 72 away from the side close to the distal end 76a of the swing member 76. The compression spring 212 also functions as a coupling member to couple the distal end portion 72a of the first grasping member 72 to the distal end 76a of the swing member 76.

Instead of the compression spring 212 shown in FIG. 8A, for example, a columnar resin material (elastic member) having a similar elastic function may be used.

Figure 8B:
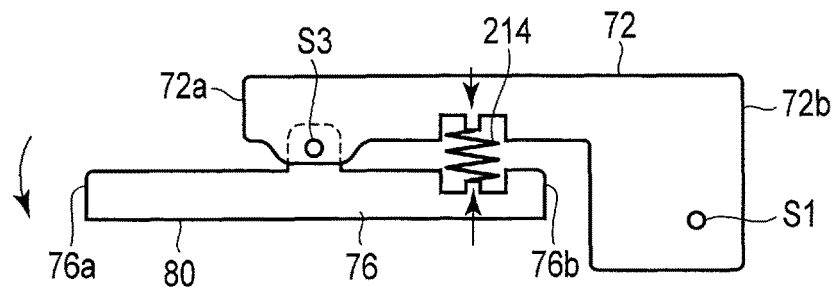
FIG. 8B is a schematic diagram showing the relation between the first grasping member and the swing member of the treatment portion of the treatment device according to the second embodiment, and showing how the proximal end portion of the first grasping member is coupled to the proximal end of the swing member by a tension spring.

The treatment portion 26 shown in FIG. 8B has a tension spring 214 disposed between the proximal end portion 72b of the first grasping member 72 and the proximal end 76b of the swing member 76. The tension spring 214 urges the proximal end 76b of the swing member 76 to move farther away from the second grasping member 74 than the distal end 76a of the swing member 76 by the proximal end portion 72b of the first grasping member 72. That is, the tension spring 214 is disposed between the side closer to the proximal end portion 72b of the first grasping member 72 than the support shaft S3 and the side close to the proximal end 76b of the swing member 76, and brings the side close to the proximal end portion 72b of the first grasping member 72 away from the side close to the proximal end 76b of the swing member 76. The tension spring 214 also functions as a coupling member to couple the proximal end portion 72b of the first grasping member 72 to the proximal end 76b of the swing member 76.

Instead of the tension spring 214 shown in FIG. 8B, for example, a columnar resin material (elastic member) having a similar elastic function may be used.

Figure 8C:
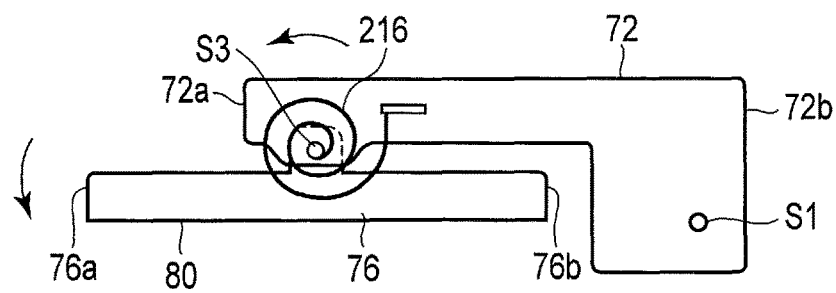
FIG. 8C is a schematic diagram showing the relation between the first grasping member and the swing member of the treatment portion of the treatment device according to the second embodiment, and showing how a torsion spring is provided in the support shaft of the first grasping member and the swing member so that an urging force can be generated to bring the distal end of the swing member closer to the second holding surface and to bring the proximal end of the swing member away from the second holding surface.

The treatment portion 26 shown in FIG. 8C has a torsion spring (elastic member) 216 disposed on the support shaft S3 of the first grasping member 72 and the swing member 76. The torsion spring 216 urges the distal end 76a of the swing member 76 to come closer to the second grasping member 74 than the proximal end 76b of the swing member 76, and urges the proximal end 76b of the swing member 76 to move farther away from the second grasping member 74 than the distal end 76a of the swing member 76. The torsion spring 216 also functions as a coupling member to couple the first grasping member 72 to the swing member 76.

Figure 8D:
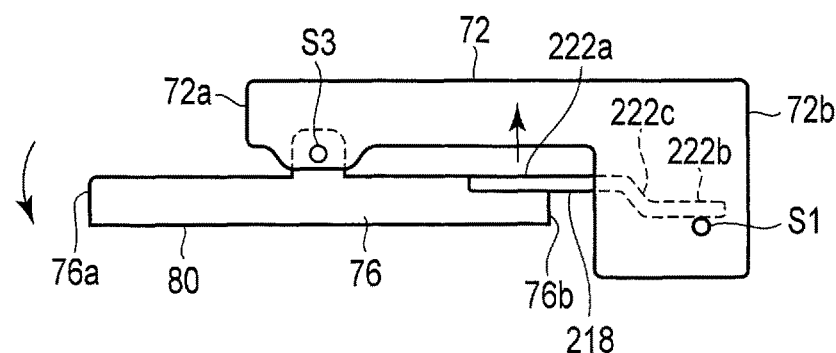
FIG. 8D is a schematic diagram showing the relation between the first grasping member and the swing member of the treatment portion of the treatment device according to the second embodiment, and showing how the proximal end portion of the first grasping member is coupled to the proximal end of the swing member by a leaf spring so that the urging force can be generated to bring the distal end of the swing member closer to the second holding surface and to bring the proximal end of the swing member away from the second holding surface.

The treatment portion 26 shown in FIG. 8D has a leaf spring (elastic member) 218 disposed on the swing member 76 and the swing supporting point S1. The leaf spring 218 according to this embodiment has, for example, a first surface 222a coupled to the swing member 76, a second surface 222b coupled to the swing supporting point S1, and a third surface 222c disposed between the first and second surfaces 222a and 222b. The first surface 222a urges the proximal end 76b of the swing member 76 to move farther away from the second grasping member 74 than the distal end 76a. The leaf spring 218 also functions as a coupling member to couple the first grasping member 72 to the swing member 76. In addition, the first and second surfaces 222a and 222b are formed, for example, substantially parallel in a no-load state as shown in FIG. 8D. The third surface 222c is formed as an inclined surface which is inclined relative to the first and second surfaces 222a and 222b.

The functions of the examples shown in FIG. 8A to FIG. 8D are described in connection with the representative example in which the leaf spring 218 shown in FIG. 8D is disposed.

As shown in FIG. 9A, the first grasping member 72 is closed relative to the second grasping member 74. As shown in FIG. 9B, due to the operation of the leaf spring 218, the proximal end 76b of the swing member 76 is raised closer to the proximal end portion 72b of the first grasping member 72, and the distal end 76a of the swing member 76 comes close to the second grasping member 74 earlier than the proximal end 76b. As shown in FIG. 9C, when the swing member 76 is completely closed relative to the second grasping member 74, the first holding surface 80 of the swing member 76 and the second holding surface 82 of the second grasping member 74 become parallel due to the operation of the leaf spring 218.

The protrusion 88 does not need to be provided in the second holding surface 82, and it is also preferable that the protrusion 88 is provided in the first holding surface 80 as shown in FIG. 9A to FIG. 9C. That is, the protrusion 88 has only to be provided in at least one of the first and second holding surfaces 80 and 82.

In the example described above according to the first embodiment (see FIG. 6A to FIG. 6C), the living tissue $L_T$ is located at the position closer to the proximal end 76b than the middle part between the distal end 76a and the proximal end 76b of the swing member 76. In the case where the elastic member is used for the treatment portion 26 described in the first embodiment as in the examples shown in the second embodiment (FIG. 8A to FIG. 8D), the distal end 76a of the swing member 76 can be brought close to the second holding surface 82 earlier than the proximal end 76b when the first holding surface 80 is closed relative to the second holding surface 82 even if the living tissue $L_T$ is located at the position close to the middle part between the distal end 76a and the proximal end 76b of the swing member 76 or close to the proximal end 76b. That is, when the first holding surface 80 shown in FIG. 8A to FIG. 8C is closed relative to the second holding surface 82, the living tissue $L_T$ may be located in the middle part between the distal end 76a and the proximal end 76b of the swing member 76, at the position close to the distal end 76a, or at the position close to the proximal end 76b. In other words, when the first holding surface 80 shown in FIG. 8A to FIG. 8C is closed relative to the second holding surface 82, the distal end 76a of the swing member 76 can be brought close to the second holding surface 82 earlier than the proximal end 76b even if the living tissue is located at any position between the distal end 76a and the proximal end 76b of the swing member 76.

Next, the third embodiment is described with reference to FIG. 10A and FIG. 10B. This embodiment is a modification of the first and second embodiments. The same components as the components described in the first and second embodiments or the components having the same functions are provided with the same signs wherever possible, and detailed explanations thereof are omitted.

As shown in FIG. 10A and FIG. 10B, a covering member 232 may be disposed on the outer circumference of the first grasping member 72 of the treatment portion 26. The covering member 232 covers the part of the first grasping member 72 opposite to the swing member 76. That is, the covering member 232 covers the part of the distal end 76a of the swing member 76 opposite to the first holding surface 80. This covering member 232 has a cavity area 234 between the covering member 232 and the distal end 76a of the swing member 76. Thus, the cavity area 234 of the covering member 232 functions as a heat insulating portion, so that when, for example, high-frequency energy is applied to the living tissue, it is possible to prevent the heat from the first holding surface 80 from escaping to the outside through the swing member 76 and the first grasping member 72. In other words, the covering member 232 covers the part of the first grasping member 72 opposite to the swing member 76, so that a temperature increase in the outer surface of the first grasping member 72 (the side of the first grasping member 72 opposite to the swing member 76) can be inhibited by the heat insulating properties of the covering member 232 even if the heat from the first holding surface 80 is transmitted to the outside through the swing member 76 and the first grasping member 72.

In the examples described in the first to third embodiments, the first high-frequency electrode 84 is present in the first holding surface 80, and the second high-frequency electrode 86 is disposed in the second holding surface 82. However, no first and second high-frequency electrodes (energy applying portions) 84 and 86 may be disposed. In this embodiment, the cutter 54 and the cutter guide grooves 152 and 154 are not always necessary. The high-frequency electrodes 84 and 86 are not exclusively substantially U-shaped, and can be any suitable shape.

Although the first and second high-frequency electrodes 84 and 86 in the treatment instrument 12 described according to the first to third embodiments are bipolar types, the first and second high-frequency electrodes 84 and 86 may be monopolar types which are used so that an unshown return electrode is attached to a patient.

Although the treatment device 12 in which the thin plate-shaped high-frequency electrodes 84 and 86 are respectively disposed in the holding surfaces 80 and 82 is described in the examples according to the first to third embodiments, thin plate-shaped heaters (energy applying portions) may be used instead of the high-frequency electrodes 84 and 86. Alternatively, thin plate-shaped heaters disposed on the rear surfaces of the thin plate-shaped high-frequency electrodes 84 and 86 may be used.

Although the cutter driving knob 34 is operated to advance or retreat the cutter 54 in the examples described according to the first to third embodiments, the treatment assistive device is not limited to the cutter as long as the treatment assistive device is used to assistive in a treatment. For example, an ultrasonically vibrating probe may be used instead of the cutter 54.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment device configured to hold a living tissue, the treatment device comprising:
   first and second grasping members configured to open and close relative to each other, each of first and second grasping members including a distal end portion, a proximal end portion, and a longitudinal axis defined by the distal end portion and the proximal end portion;
   a support shaft configured to extend in a direction perpendicular to the longitudinal axis and in a direction that intersects at right angles with an open-close direction of the first and second grasping members;
   a pivot pin connected to the proximal end portion of the first grasping member;
   a swing member including a distal end, a proximal end, and a middle position between the distal end and the proximal end, wherein:
       the first grasping member is configured to couple with a portion of the swing member at a point along a coupling portion of the swing member, the coupling portion of the swing member extends from the distal end of the swing member to the middle position of the swing member, and the swing member is configured to rotate in a first direction and in a second direction opposite the first direction on the support shaft;

a first holding surface which is provided on the swing member close to a side of the second grasping member and which is configured to hold the living tissue;

a second holding surface which is provided on the second grasping member close to a side of the swing member and which faces the first holding surface and which is configured to hold the living tissue in cooperation with the first holding surface of the swing member; and a coupling member including a plate spring having:
- a distal portion configured to connect the plate spring with the proximal end of the swing member;
- a proximal portion configured to connect the plate spring with the pivot pin; and
- a crank portion disposed between the distal portion and the proximal portion; and the coupling member being configured to couple the first grasping member to the swing member and which rotates the distal end of the swing member on the support shaft toward the second grasping member when the first grasping member is closed relative to the second grasping member.

2. The treatment device according to claim 1, the plate spring being provided between a side closer to the proximal end portion of the first grasping member than the support shaft and a side close to the proximal end of the swing member, the plate spring bringing the side close to the proximal end portion of the first grasping member closer to the side close to the proximal end of the swing member.

3. The treatment device according to claim 1, further comprising: an energy applying portion which is provided in at least one of the first and second holding surfaces and which is configured to apply energy to the living tissue held between the first and second holding surfaces; and a protrusion which is provided in at least one of the first and second holding surfaces and which forms a clearance between the first and second holding surfaces when the first and second holding surfaces are closed relative to each other.

4. The treatment device according to claim 1, wherein the first grasping member includes a covering portion which covers a part opposite the swing member, the covering portion allowing heat from the first holding surface to be transmitted to the outside through the swing member and the first grasping member, and inhibiting a temperature increase in the outer surface of the first grasping member.

5. The treatment device according to claim 4, wherein the covering portion covers the side of the distal end of the swing member opposite the first grasping member, and includes a cavity area between the covering portion and the distal end of the swing member.

6. The treatment device according to claim 1, further comprising: a treatment assistive device movable between a position located between the swing member and the second grasping member and a position to move away from the position located between the swing member and the second grasping member; a first guide groove which is provided in the first holding surface and which is configured to guide the treatment assistive device between the first and second holding surfaces; and a second guide groove which is provided in the second holding surface and which is configured to guide the treatment assistive device in cooperation with the first guide groove.

* * * * *